United States Patent [19]

Sugo

[11] Patent Number: 5,641,482

[45] Date of Patent: Jun. 24, 1997

[54] DEODORIZING MATERIAL FOR ANIMAL BREEDING AND PROCESS FOR PRODUCING THE SAME

[76] Inventor: Tetsuko Sugo, 186-5, Ushirobikima, Gunmamachi, Gunma-gun, Gunma-ken, Japan

[21] Appl. No.: 358,989

[22] Filed: Dec. 19, 1994

Related U.S. Application Data

[63] Continuation of Ser. No. 693,540, Apr. 30, 1991, abandoned.

[30] Foreign Application Priority Data

Mar. 18, 1991 [JP] Japan .................................. 3-052253

[51] Int. Cl.$^6$ .................................. A61K 31/74; A61L 11/00
[52] U.S. Cl. .................................. 424/76.6; 424/78.1; 119/171
[58] Field of Search .................................. 424/76.6, 78.1

[56] References Cited

U.S. PATENT DOCUMENTS

| | | | |
|---|---|---|---|
| 2,955,067 | 10/1960 | McBurney | 521/30 |
| 3,553,306 | 1/1971 | Ehwich | 521/30 |
| 3,860,414 | 1/1975 | Lang et al. | 75/34 |
| 4,255,533 | 3/1981 | Bartz | 525/71 |
| 4,506,628 | 3/1985 | Stockel | 119/173 |
| 4,517,919 | 5/1985 | Benjamin et al. | 119/302 |
| 4,685,420 | 8/1987 | Stuart | 119/1 |
| 4,959,207 | 9/1990 | Ueda et al. | 422/5 |

FOREIGN PATENT DOCUMENTS

| | | | |
|---|---|---|---|
| 0042075 | 5/1981 | European Pat. Off. . | |
| 0117478 | 2/1984 | European Pat. Off. . | |
| 0154465 | 11/1985 | European Pat. Off. | 424/65 |
| 2069123 | 5/1988 | Japan | 119/171 |
| 269123 | 9/1988 | Japan . | |
| WOA8903694 | 5/1989 | Japan . | |
| 1282396 | 11/1989 | Japan | 521/30 |
| 901039 | 10/1958 | United Kingdom . | |
| 1530649 | 10/1976 | United Kingdom . | |
| 1600161 | 3/1978 | United Kingdom . | |
| 2030990 | 9/1979 | United Kingdom . | |
| 2074173 | 4/1981 | United Kingdom . | |

OTHER PUBLICATIONS

Journal of the Society of the Cosmetic Chemists May 1956 pp. 256–267.

*Primary Examiner*—Peter F. Kulkosky
*Attorney, Agent, or Firm*—Fish & Richardson PC

[57] ABSTRACT

A deodorizing material for breeding or keeping animals and a process for producing the same are described. The material comprises a formed article of a pulp and/or polyolefin base material, wherein said formed article has a cation exchange group. The material is produced by graft polymerization of a reactive monomer having a cation exchange group to a formed article of a pulp and/or polyolefin base material. The material efficiently adsorbs bad smells of animals' excretions through chemical bonding.

2 Claims, No Drawings

DEODORIZING MATERIAL FOR ANIMAL BREEDING AND PROCESS FOR PRODUCING THE SAME

This application is a continuation of U.S. application Ser. No. 07/693,540, filed Apr. 30, 1991, now abandoned.

FIELD OF THE INVENTION

This invention relates to a material useful for improving living environment, and more particularly to a material useful for deodorization for animal breeding or keeping and a process for producing the same.

BACKGROUND OF THE INVENTION

Animal breeding or keeping is accompanied with an offensive smell mainly comprising ammonia, triethylamine, and sulfides. Deodorization in animal breeding or keeping has been effected with adsorbents, such as activated carbon, zeolite, bentonire, and impregnated pulp, and deodorant sprays. In keeping, e.g., cats indoors, since excrements of cats give off an awful smell, zeolite, bentonire, siliceous sand, etc. are used as toilet sand, which is disposed after each use. However, if these non-combustible materials are disposed together with combustible garbage, such would be a cause of obstruction of public facilities of garbage incineration, giving rise to a serious social problem.

Impregnated pulp, which has recently been extending its use because of its combustibility, has poor deodorizing effects. Moreover, since it is easily electrified, it adheres to the paws, making the floor dirty. The same disadvantage also applies to activated carbon.

Deodorant sprays only show a slight masking effect, furnishing no fundamental means of deodorization.

Thus, the problem of smell associated with animal breeding or keeping has not yet come to a satisfactory solution. Besides the problem of domestic animals, in cities of growing population, there is an increasing demand for a solution to the problem of smell of laboratory animals from the standpoint of environmental hygiene in the neighborhood.

SUMMARY OF THE INVENTION

In the light of the above-described situation, an object of the present invention is to provide a material capable of effectively removing bad odors of outputs and excrements of animals and a process for producing such a material.

The inventors have conducted extensive investigations and, as a result, it has now been found that the above object of the present invention is accomplished by a formed article of a pulp and/or polyolefin base material, said formed article having a cation exchange group.

DETAILED DESCRIPTION OF THE INVENTION

The base material which can be used in the present invention comprises pulp and/or a polyolefin, such as paper pulp, regenerated paper, polyethylene, and polypropylene. The base material to be used can be appropriately selected from among them according to the end use. The base material preferably has a fibrous form for assuring a wider surface area, which leads to an increased rate of adsorption of harmful substances, and ease of forming into any desired shape. The fibers preferably have a diameter of from 1 to 50 μm. With the fiber diameter being within this range, graft polymerization takes place uniformly over the cross-section of fibers.

A formed article comprising the base material has an aggregate form, such as mat, non-woven fabric, or a mass of spheres or flakes. For use as a toilet for cats, spherical or flaky formed articles are preferred for making it easy for cats to dig in as their habit. The spherical or flaky formed articles preferably have a size of from 2 to 20 mm. If they have too a large size, it is likely that family animals like cats play with them and bring them out of the toilet.

A reactive monomer is graft-polymerized to the formed article to introduce a cation exchange group. The reactive monomer which can be used in the present invention include those having a cation exchange group or a group capable of being converted to a cation exchange group. Examples of such reactive monomers are glycidyl methacrylate, glycidyl acrylate, styrene, and sodium styrenesulfonate. Examples of suitable cation exchange groups include a carboxyl group, a sulfo group, and a phospho group. The cation exchange group is preferably introduced into the formed article in an amount of from 0.5 to 8 mmol/g.

Graft polymerization of the reactive monomer to the formed article can be carried out, for example, by polymerization in the presence of an initiator, thermal polymerization, irradiation-induced polymerization using ionizing radiation, e.g., α-rays, β-rays, γ-rays, accelerated electron rays, X-rays, and ultraviolet rays. Polymerization induced by γ-rays or accelerated electron rays is suitable for practical use.

The amount of a reactive monomer polymerized on the formed article is expressed in terms of grafting rate (%) obtained from equation:

$$\text{Grafting Rate} = \frac{\text{Weight after grafting} - \text{Weight before grafting}}{\text{Weight before grafting}} \times 100$$

In the present invention, a grafting rate preferably ranges from 10 to 150%. If the grafting rate is out of this range, performance properties characteristic of the base material tend to be impaired.

Modes of graft polymerization of a reactive monomer to a formed article are divided into liquid phase polymerization in which a formed article is directly reacted with a liquid reactive monomer and gaseous phase polymerization in which a formed article is brought into contact with vapor or gas of a reactive monomer. Either of these modes of polymerization can be chosen in the present invention according to the end use or purpose.

Substances giving off a bad smell of ammonia, triethylamine, etc. can be removed on neutralization reaction with a strongly acidic cation exchange group. That is, the deodorizing material according to the present invention achieves deodorization predominantly through chemical adsorption without being accompanied by desorption of the smell irrespective of environmental changes, whereas most of conventional inorganic adsorbents conduct deodorization through physical adsorption and are therefore liable to release once adsorbed substances depending on environmental changes. In addition, the deodorizing material of the present invention is easily regenerated by washing or a like means for reuse.

The present invention is now illustrated in greater detail with reference to the following Examples, but it should be understood that the present invention is not construed as being limited thereto. All the percents, parts, and ratios are by weight unless otherwise indicated.

EXAMPLE 1

Regenerated paper pulp flakes having an average diameter of 5 mm were soaked in the same volume of a glycidyl methacrylate solution for 10 minutes. After the excess liquid was removed, the impregnated flakes were placed in an irradiation chamber. After rendering the chamber oxygen-free, cobalt 60 γ-rays were irradiated on the flakes at an absorption dose of 1 Mrad to induce graft polymerization to obtain a graft polymer. The resulting polymer was washed with dimethylformamide and then immersed in a 10% propanol-water solution of sodium sulfite at 80° C. for 5 hours to conduct sulfonation. There was obtained a deodorizing material containing 2.5 mmol of a sulfo group per gram of the base material.

A hundred parts by weight of commercially available toilet sand for cats were mixed with 10 parts by weight of the resulting deodorizing material, and the mixed sand was placed in a room having a floor space of about 10 m$^2$ where a cat was allowed to excrete. After one day, a pungent smell of the cat's excrements was imperceptible 1 m apart from the toilet sand. At this time, the ammonia concentration in the atmosphere 1 cm apart from the surface of the toilet sand was 0.2 ppm as measured with a gas detector. After 2 weeks, the toilet slightly smelled at 1 m distance. At this time, the ammonia concentration at 1 cm distance from the toilet sand was 0.5 ppm as measured with a gas detector.

For comparison, the same test was carried out using toilet sand containing no deodorizing material of the invention. After 1 day, the cat's excrements irritatingly smelled all over the room, and the ammonia concentration 1 cm distant from the surface of the toilet sand was 2 ppm as measured with a gas detector. After three days, the smell was so irritant that one could not stay any more in that room with all the windows and doors shut. The toilet was moved to another place, but the awful smell still remained in the room event after one night had elapsed. So, 30 g of the above prepared deodorizing material packaged in a net was suspended in the center of the room. One day after the suspension, the room had no bad smell at all.

From these results, the deodorizing material of the present invention was proved to produce remarkable deodorizing effects when used either alone or in combination with conventional toilet sand.

EXAMPLE 2

Polypropylene fibers having a diameter of 20 μm were formed into spheres having an average diameter of 5 mm. Accelerated electron rays were irradiated on the spheres in a nitrogen atmosphere at a dose of 10 Mrad by means of an electron beam accelerator. The irradiated spheres were brought into contact with an oxygen-free acrylic acid solution for 2 hours to conduct graft polymerization, followed by washing with a large quantity of warm water. There was obtained a deodorizing material containing 5.6 mmol of a carboxyl group per gram of the base material.

Thirty grams of the resulting deodorizing material were put in a nest box of hamster. After one day, the ammonia concentration in the box was 0.2 ppm as measured with a gas detector. Even after one week, it was not more than 0.5 ppm.

For comparison, when the same test was conducted without using the deodorizing material of the present invention, the ammonia concentration after one day was 1.2 ppm, clearly demonstrating the adsorptive effects of the deodorizing material of the present invention.

While the invention has been described in detail and with reference to specific examples thereof, it will be apparent to one skilled in the art that various changes and modifications can be make therein without departing from the spirit and scope thereof.

What is claimed is:

1. An animal toilet composition consisting essentially of formed articles of a base material having a side chain with a cation exchange group, said articles being formed from a process involving radiation graft-polymerizing a reactive monomer onto the base material, wherein:

(a) said base material comprises pulp and/or polypropylene;
   (b) said reactive monomer being selected from the group consisting of glycidyl methacrylate, and acrylic acid;
   (c) said formed article being a spherical or flaky formed article having a size from 2 to 20 mm; and
   (d) said base material consisting essentially of fibers having a fiber diameter from 1 to 50 μm;
   said formed articles being effective to reduce ammonia concentration.

2. A process for producing an animal toilet composition consisting essentially of formed articles of a base material upon which has been radiation graft-polymerized a reactive monomer so as to provide a side chain on the base material, and introducing a cation exchange group to the graft-polymerized side chain of the base material, wherein:

(a) said base material comprises pulp and/or polypropylene;
   (b) said reactive monomer being selected from the group consisting of glycidyl methacrylate, and acrylic acid;
   (c) said formed article being a spherical or flaky formed article having a size from 2 to 20 mm; and
   (d) said base material consisting essentially of fibers having a fiber diameter from 1 to 50 μm;
   said formed articles being effective to reduce ammonia concentration.

* * * * *

UNITED STATES PATENT AND TRADEMARK OFFICE
CERTIFICATE OF CORRECTION

PATENT NO.   : 5,641,482

DATED        : June 24, 1997

INVENTOR(S)  : Etsuko Sugo

It is certified that error appears in the above-identified patent and that said Letters Patent is hereby corrected as shown below:

```
On the title page, item [19] & [76]
     Inventor, line 1, "Tetsuko Sugo" should be --Etsuko
                          Sugo--.
```

Signed and Sealed this

Tenth Day of March, 1998

Attest:

BRUCE LEHMAN

Attesting Officer

Commissioner of Patents and Trademarks